(12) United States Patent
Sowden

(10) Patent No.: US 7,530,804 B2
(45) Date of Patent: *May 12, 2009

(54) SYSTEM AND PROCESS FOR PROVIDING AT LEAST ONE OPENING IN DOSAGE FORMS

(75) Inventor: Harry S. Sowden, Glenside, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 799 days.

This patent is subject to a terminal disclaimer.

(21) Appl. No.: 11/006,038

(22) Filed: Dec. 7, 2004

(65) Prior Publication Data

US 2006/0118991 A1   Jun. 8, 2006

(51) Int. Cl.
*B29C 71/02* (2006.01)
*B30B 11/08* (2006.01)

(52) U.S. Cl. .......................... 425/112; 83/879; 83/883; 425/289; 425/445

(58) Field of Classification Search ................. 425/112, 425/289, 445; 83/879, 883
See application file for complete search history.

(56) References Cited

U.S. PATENT DOCUMENTS

| | | | |
|---|---|---|---|
| 3,185,626 A | 5/1965 | Baker | |
| 3,823,816 A | 7/1974 | Controulis et al. | |
| 4,271,113 A * | 6/1981 | Luschen | 264/112 |
| 4,449,983 A | 5/1984 | Cortese et al. | |
| 4,543,370 A | 9/1985 | Porter et al. | |
| 4,576,604 A | 3/1986 | Guittard et al. | |
| 4,643,894 A | 2/1987 | Porter et al. | |
| 4,683,256 A | 7/1987 | Porter et al. | |
| 4,725,441 A | 2/1988 | Porter et al. | |
| 4,802,924 A | 2/1989 | Woznicki et al. | |
| 4,820,524 A | 4/1989 | Berta | |
| 4,828,841 A | 5/1989 | Porter et al. | |
| 5,071,607 A * | 12/1991 | Ayer et al. | 264/112 |
| 5,089,270 A | 2/1992 | Hampton et al. | |
| 5,146,730 A | 9/1992 | Sadek et al. | |
| 5,200,192 A | 4/1993 | Wimmer | |
| 5,213,738 A | 5/1993 | Hampton et al. | |
| 5,228,916 A | 7/1993 | Berta | |
| 5,256,440 A | 10/1993 | Appel et al. | |
| 5,415,868 A | 5/1995 | Smith et al. | |
| 5,436,026 A | 7/1995 | Berta | |
| 5,459,983 A | 10/1995 | Sadek et al. | |
| 5,464,631 A | 11/1995 | Hoover et al. | |
| 5,511,361 A | 4/1996 | Sauter | |
| 5,538,125 A | 7/1996 | Berta | |
| 5,609,010 A | 3/1997 | Sauter | |
| 5,630,871 A | 5/1997 | Jordan | |
| 5,679,406 A | 10/1997 | Berta | |

(Continued)

OTHER PUBLICATIONS

Hard Capsule Development, pp. 77-78, K. Ridgway (1987).

(Continued)

*Primary Examiner*—Yogendra Gupta
*Assistant Examiner*—Emmanuel S Luk

(57) ABSTRACT

The present invention relates to apparatus, methods, and processes for making solid dosage forms comprising at least one active ingredient, a core and shell configuration, wherein the shell comprises a hardenable material, such as a thermal-gelling polymer, for example gelatin; and the shell is provided with at least one opening. The opening(s) are formed while the shell is still in a softened state.

24 Claims, 9 Drawing Sheets

U.S. PATENT DOCUMENTS

| | | |
|---|---|---|
| 5,795,588 A | 8/1998 | Sauter |
| 5,824,338 A | 10/1998 | Jacobs et al. |
| 5,942,034 A | 8/1999 | Brehant et al. |
| 6,274,162 B1 | 8/2001 | Steffenino et al. |
| 6,767,200 B2 | 7/2004 | Sowden et al. |
| 7,404,708 B2 * | 7/2008 | Sowden ............ 425/112 |
| 2003/0068367 A1 | 4/2003 | Sowden et al. |
| 2003/0086973 A1 | 5/2003 | Sowden et al. |

OTHER PUBLICATIONS

U.S. Appl. No. 10/677,984, Anderson et al.

* cited by examiner

SYSTEM AND PROCESS FOR PROVIDING AT LEAST ONE OPENING IN DOSAGE FORMS

SUMMARY OF THE INVENTION

The present invention relates to apparatus, methods, and processes for making solid dosage forms comprising at least one active ingredient, a core and shell configuration, wherein the shell comprises a hardenable material, such as a thermal-gelling polymer, for example gelatin; and the shell is provided with at least one opening. The opening(s) are formed while the shell is still in a softened state.

BACKGROUND

A variety of dosage forms, such as tablets, capsules and gelcaps are known in the pharmaceutical arts. Tablets generally refer to relatively compressed powders in various shapes. One type of elongated, capsule-shaped tablet is commonly referred to as a "caplet." Capsules are typically manufactured using a two piece gelatin shell formed by dipping a steel rod into gelatin so that the gelatin coats the end of the rod. The gelatin is hardened into two half-shells and the rod extracted. The hardened half-shells are then filled with a powder and the two halves joined together to form the capsule.

Dosage forms having core and shell portions are well-known. Outer shell portions are provided over active cores for many reasons. The shell can, for example, provide taste-masking of bitter actives, modify the dissolution profile, delay the delivery thereof, or provide means for identifying the sources of goods.

Gelatin-coated tablets, commonly known as geltabs and gelcaps, are an improvement on gelatin capsules and typically comprise a tablet coated with a gelatin shell. Several well known examples of gelcaps are McNeil Consumer Healthcare's acetaminophen based products sold under the trade name Tylenol®. U.S. Pat. Nos. 4,820,524; 5,538,125; 5,228,916; 5,436,026; 5,679,406; 5,415,868; 5,824,338; 5,089,270; 5,213,738; 5,464,631; 5,795,588; 5,511,361; 5,609,010; 5,200,191; 5,459,983; 5,146,730; 5,942,034 describe geltabs and gelcaps and methods and apparatuses for making them. Conventional methods for forming gelcaps are generally performed in a batchwise manner using a number of stand alone machines operating independently. Such batch processes typically include the unit operations of granulating, drying, blending, compacting (e.g., in a tablet press), gelatin dipping or enrobing, drying, and printing.

Another method of producing gelatin coated dosage forms is via an enrobing process wherein two separate films made of gelatinous material are applied to opposite sides of a tablet by a pair of rotary dies, as disclosed for example, in U.S. Pat. Nos. 5,146,730 and 5,459,983. Film formulations for producing gelcaps and geltabs prepared via enrobing methods such as those disclosed in U.S. Pat. Nos. 5,146,730 and 5,459,983 typically comprise a water-based gelatin preparation having about 45% gelatin and about 9% plasticizer (glycerin and/or sorbitol) by weight. Glycerin and sorbitol can be used as single plasticizers or in combination with each other. In addition, other sugars and poly-hydroxy compounds can be used as additives and plasticizers. If a tamper-evident gelatin-coated medicine tablet is the desired end product, then the ratio of plasticizer to gelatin in the gelatin formulation should be in the range of about 1:5.

Certain dosage forms containing apertures or embossments are known. For instance, "osmotic pump" dosage forms for the administration of pharmaceutically active ingredients are known in the art. They typically comprise a semi-permeable wall that surrounds a reservoir containing drug. The wall is permeable to the passage of an external fluid, impermeable to the passage of drug, and has a passageway through the semipermeable wall for delivering drug from the osmotic system. For example, U.S. Pat. No. 4,576,604 discloses an osmotic device comprising a drug compartment surrounded by a wall (coating) having a passageway therein. The wall may comprise an immediate release dose of drug, and the inner drug compartment may comprise a sustained release dose of drug.

U.S. Pat. No. 4,449,983 discloses another osmotic device comprising two separately housed drugs that are separately dispensed from the device. The device comprises two compartments, one for each drug, separated by a partition. Each compartment has an orifice for communicating with the exterior of the device.

U.S. Pat. No. 3,823,816 discloses a water-soluble package provided in the form of a hard shell capsule filled with powder, granules, or the like. The capsule is apertured, and a water-soluble barrier film covers the apertures. The film is more water soluble than the capsule so that when the package contacts water, the film rather than the capsule dissolves first, exposing the contents for dissolution and/or release by way of the apertures while the capsule is intact.

U.S. Pat. No. 5,256,440 relates to an intagliated dosage form comprising one or more circumscribed regions on its surface. The dosage form is spray coated with a latex polymer. When placed in an environment of use, the latex coating within the circumscribed region is reproducibly expelled, leaving a coated core tablet with a predefined aperture, which exposes a discrete portion of the core surface to the environment of use.

SUMMARY OF THE INVENTION

The present invention is directed to a system for manufacturing one or more dosage forms having a core and a shell that surrounds at least a portion of the core and having one or more openings. The system comprises a shell-forming module that overcoats at least a portion of the core with a soft shell, a post-coating transfer module for conveying a soft dosage form from the shell-forming module, and a punch assembly for producing at least one opening in the soft shell. The system can further comprise a hardening module for substantially solidifying the shell.

The hardening module can employ a drying module for substantially eliminating moisture from the shell. The post-coating transfer module can include a substrate velocity modifying means that enables a controlled transfer of individual substrates between two unit operations that convey individual substrates at different velocities. The post-coating transfer module can be characterized by having a first dosage form conveyor from the shell-forming module, a substrate velocity modifying means for modifying the velocity of dosage forms received from the first dosage form conveyor and a second dosage form conveyor from the substrate velocity modifying means. A transfer arm can move dosage forms from the second conveyor to a third conveyor into a dryer unit.

The substrate velocity modifying means can be characterized as having a rotating turret with a plurality of slats for holding individual dosage form carriers. Each slat preferably comprises two carrier tubes. The carrier tubes can move from the outer periphery of the rotating turret towards the center of the rotating turret. Alternatively, the carrier tubes move closer to one another in a radial direction.

The soft shell dosage form preferably has a water-content at least 20% greater than its moisture content at equilibrium at 25° C. and 60% relative humidity. The shell can contain one or more gelatin or gelling materials. The average thickness of the shell, excluding uncoated or exposed areas of the core, is preferably in the range from about 100 to about 400 microns. The core comprises at least one active ingredient that can be provided for immediate release. The core can be in the form of a compressed tablet, preferably having a hardness from about 1 to about 30 kp/cm$^2$. One or more openings can be provided into or through the shell, each opening can be from about 200 to about 2000 microns in diameter (if circular) or provide similar a similar opening area regardless of the shape of the opening.

The post-coating transfer module can convey a soft dosage form from the shell-forming module to the punch assembly for producing at least one opening in the soft shell. The punch assembly can be located along the path of the first dosage form conveyor, adjacent to the means for modifying dosage form velocity, along the path of the second conveyor or along the path of the third conveyor.

The present invention is also directed to a process for making a dosage form having a core and a shell that surrounds at least a portion of the core and having one or more openings. The process comprises providing a shell over at least a portion of the compressed core and providing at least one opening in said shell, wherein the shell is soft at the time the opening is provided in said shell. One or more openings through the shell can contact the core. The soft shell preferably has, at a point in time immediately before one or more openings are provided therein, a water-content at least 20% greater than its moisture content at equilibrium at 25° C. and 60% relative humidity.

The present invention is particularly advantageous for providing openings through outer coatings comprising gelatin. Dry gelatin, such as that in hard gelatin capsule shells or finished gelcap coatings cannot be ablated using lasers due to scorching. Forming openings by punching while the gelatin is still in a hydrated (soft and deformable) state allows for both an easier punch through and some smoothing of the edges of the punched opening due to cold flow.

DETAILED DESCRIPTION OF THE INVENTION

The present invention is directed to apparatus, methods, and processes for making solid dosage forms comprising at least one active ingredient, a core and shell configuration, wherein the shell comprises a hardenable material, such as a thermal-gelling polymer, for example gelatin; and the shell is provided with at least one opening. The opening(s) are formed using the method of the invention described herein. Certain materials and equipment useful in the practice of the present invention are disclosed and described more fully in U.S. Pat. No. 6,767,200, published U.S. Patent Application 2003-008367 A1, published U.S. Patent Application 2003-0086973 A1, and copending application Ser. No. 10/677,984, all of which are incorporated herein by reference.

Figure 1:
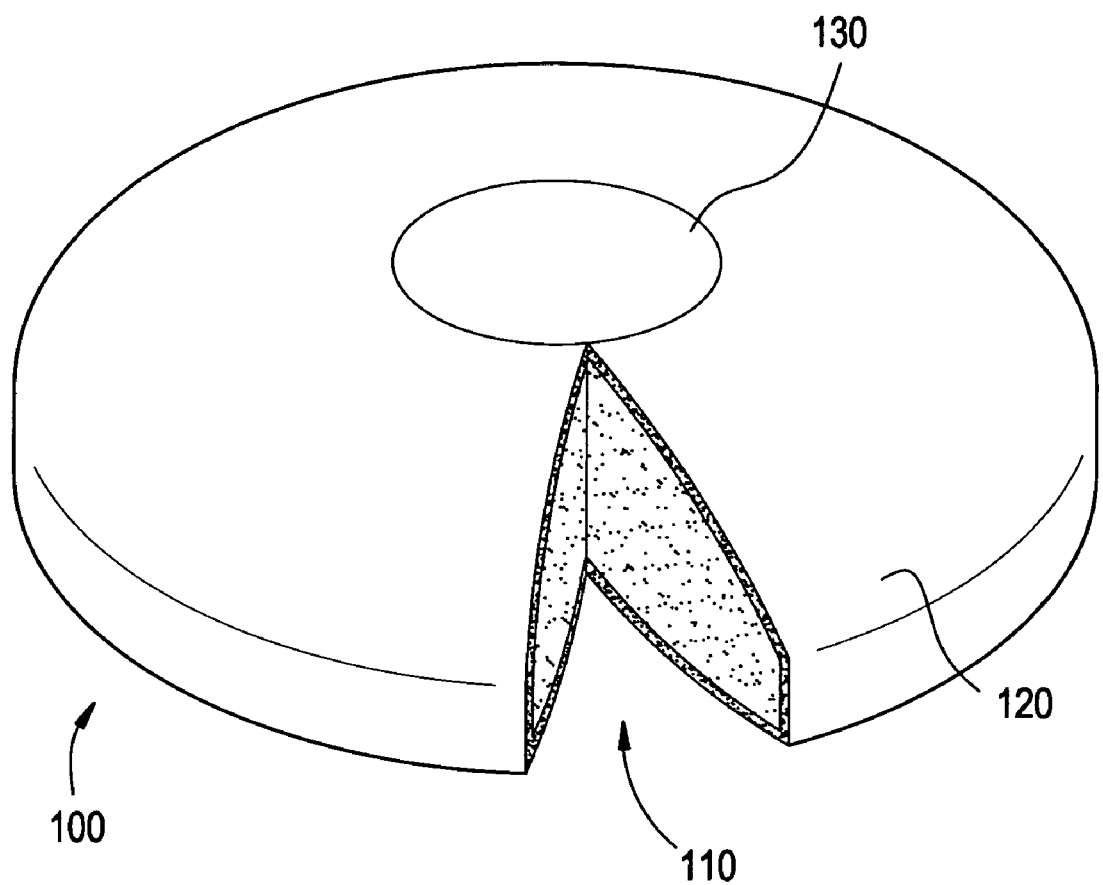
FIG. 1 is an exemplary dosage form resulting from the present invention.

An exemplary dosage form is shown in FIG. 1. Dosage form 100 comprises a core 110, a shell 120 and at least one opening 130. As used herein, the term "dosage form" applies to any solid object or semi-solid composition designed to contain a specific predetermined amount (dose) of a certain ingredient, for example an active ingredient as defined below. Suitable dosage forms may be pharmaceutical drug delivery systems, including those for oral administration, buccal administration, rectal administration, mucosal delivery, or subcutaneous implants, or other implanted drug delivery systems; or compositions for delivering minerals, vitamins and other nutraceuticals, oral care agents, flavorants, and the like. Preferably the dosage forms of the present invention are considered to be solid, however they may contain liquid or semi-solid components. In a particularly preferred embodiment, the dosage form is an orally administered system for delivering a pharmaceutical active ingredient to the gastro-intestinal tract of a human.

Suitable active ingredients for use in this invention include for example pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

In one embodiment of the invention, the active ingredient may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active ingredient is selected from analgesics, anti-inflammatories, and antipyretics, e.g. non-steroidal anti-inflammatory drugs (NSAIDs), including propionic acid derivatives, e.g. ibuprofen, naproxen, ketoprofen and the like; acetic acid derivatives, e.g. indomethacin, diclofenac, sulindac, tolmetin, and the like; fenamic acid derivatives, e.g. mefanamic acid, meclofenamic acid, flufenamic acid, and the like; biphenylcarbodylic acid derivatives, e.g. diflunisal, flufenisal, and the like; and oxicams, e.g. piroxicam, sudoxicam, isoxicam, meloxicam, and the like.

In one particular embodiment, the active ingredient is selected from propionic acid derivative NSAID, e.g. ibuprofen, naproxen, flurbiprofen, fenbufen, fenoprofen, indoprofen, ketoprofen, fluprofen, pirprofen, carpofen, oxaprozin, pranoprofen, suprofen, and pharmaceutically acceptable salts, derivatives, and combinations thereof. In another particular embodiment of the invention, the active ingredient may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment of the invention, the active ingredient may be selected from pseudoephedrine, phenylpropanolamine, chlorpheniramine, dextromethorphan, diphenhydramine, astemizole, terfenadine, fexofenadine, loratadine, desloratadine, cetirizine, mixtures thereof and pharmaceutically acceptable salts, esters, isomers, and mixtures thereof.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors must be considered, as known in the art.

Typically, the dosage form comprises at least about 1 weight percent, preferably, the dosage form comprises at least about 5 weight percent, e.g. at least about 25 weight percent of a combination of one or more active ingredients. In one preferred embodiment, a core comprises a total of at least about 50 weight percent, e.g. at least about 70 weight percent, say at least about 80 weight percent (based on the weight of the core) of one or more active ingredients.

The active ingredient or ingredients may be present in the dosage form in any form. For example, the active ingredient may be dispersed at the molecular level, e.g. melted or dissolved, within the dosage form, or may be in the form of particles, which in turn may be coated or uncoated. If the active ingredient is in form of particles, the particles (whether coated or uncoated) typically have an average particle size of about 1-2000 microns. In one preferred embodiment, such particles are crystals having an average particle size of about 1-300 microns. In another preferred embodiment, the particles are granules or pellets having an average particle size of about 50-2000 microns, preferably about 50-1000 microns, most preferably about 100-800 microns.

The core can be any solid form. The core may prepared by any suitable method, including for example compression or molding. As used herein, "core" refers to a material that is at least partially enveloped or surrounded by another material. Preferably, the core is a self-contained unitary object, such as a tablet or capsule. Typically, the core comprises a solid, for example, the core may be a compressed or molded tablet, hard or soft capsule, suppository, or a confectionery form such as a lozenge, nougat, caramel, fondant, or fat based composition.

In one embodiment the core is a compressed tablet having a hardness from about 2 to about 30 kp/cm$^2$, e.g. from about 6 to about 25 kp/cm$^2$. "Hardness" is a term used in the art to describe the diametral breaking strength of either the core or the coated solid dosage form as measured by conventional pharmaceutical hardness testing equipment, such as a Schleuniger Hardness Tester. In order to compare values across different size tablets, the breaking strength must be normalized for the area of the break. This normalized value, expressed in kp/cm$^2$, is sometimes referred in the art as tablet tensile strength. Preferably, the cores have a density of at least about 0.9 g/cc, e.g. at least about 1.0 g/cc.

The core may have one of a variety of different shapes. For example, the core may be shaped as a polyhedron, such as a cube, pyramid, prism, or the like; or may have the geometry of a space figure with some non-flat faces, such as a cone, truncated cone, cylinder, sphere, torus, or the like. In certain embodiments, a core has one or more major faces. For example, in embodiments wherein a core is a compressed tablet, the core surface typically has two opposing major faces formed by contact with the upper and lower punch faces in the compression machine. In such embodiments the core surface typically further comprises a "belly-band" located between the two major faces, and formed by contact with the die walls in the compression machine. A core may also comprise a multilayer tablet.

The core typically comprises active ingredient and a variety of excipients, depending on the method by which it is made.

In embodiments in which the core is made by compression, suitable excipients include fillers, binders, disintegrants, lubricants, glidants, and the like, as known in the art. In embodiments in which the core is made by compression and additionally confers modified release of an active ingredient contained therein, such core preferably further comprises a release-modifying compressible excipient.

Suitable fillers for use in making the core by compression include water-soluble compressible carbohydrates such as sugars, which include dextrose, sucrose, maltose, and lactose, sugar-alcohols, which include mannitol, sorbitol, maltitol, xylitol, starch hydrolysates, which include dextrins, and maltodextrins, and the like, water insoluble plastically deforming materials such as microcrystalline cellulose or other cellulosic derivatives, water-insoluble brittle fracture materials such as dicalcium phosphate, tricalcium phosphate and the like and mixtures thereof.

Suitable binders for making the core by compression include dry binders such as polyvinyl pyrrolidone, hydroxypropylmethylcellulose, and the like; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, starches, and the like; and derivatives and mixtures thereof.

Suitable disintegrants for making the core by compression, include sodium starch glycolate, cross-linked polyvinylpyrrolidone, cross-linked carboxymethylcellulose, starches, microcrystalline cellulose, and the like.

Suitable lubricants for making the core by compression include long chain fatty acids and their salts, such as magnesium stearate and stearic acid, talc, glycerides and waxes.

Suitable glidants for making the core by compression, include colloidal silicon dioxide, and the like.

In certain embodiments, the core or a portion thereof may optionally comprise release modifying excipients as known in the art. Suitable release-modifying compressible excipients for making the core by compression include swellable erodible hydrophilic materials, insoluble edible materials, pH-dependent polymers, and the like.

Suitable pharmaceutically acceptable adjuvants for making the cores by compression include, preservatives; high intensity sweeteners such as aspartame, acesulfame potassium, sucralose, and saccharin; flavorants; colorants; antioxidants; surfactants; wetting agents; and the like and mixtures thereof.

In embodiments wherein one or more cores are prepared by compression, a dry blending (i.e. direct compression), or wet granulation process may be employed, as known in the art. In a dry blending (direct compression) method, the active ingredient or ingredients, together with the excipients, are blended in a suitable blender, than transferred directly to a compression machine for pressing into tablets. In a wet granulation method, the active ingredient or ingredients, appropriate excipients, and a solution or dispersion of a wet binder (e.g. an aqueous cooked starch paste, or solution of polyvinyl pyrrolidone) are mixed and granulated. Alternatively a dry binder may be included among the excipients, and the mixture may be granulated with water or other suitable solvent. Suitable apparatuses for wet granulation are known in the art, including low shear, e.g. planetary mixers; high shear mixers; and fluid beds, including rotary fluid beds. The resulting granulated material is dried, and optionally dry-blended with further ingredients, e.g. adjuvants and/or excipients such as for example lubricants, colorants, and the like. The final dry blend is then suitable for compression.

The dry-blended, or wet granulated, powder mixture is typically compacted into tablets using a rotary compression machine as known in the art, such as for example those commercially available from Fette America Inc., Rockaway, N.J., or Manesty Machines LTD, Liverpool, UK. In a rotary compression machine, a metered volume of powder is filled into a die cavity, which rotates as part of a "die table" from the filling position to a compaction position where the powder is compacted between an upper and a lower punch to an ejection position where the resulting tablet is pushed from the die cavity by the lower punch and guided to an ejection chute by a stationary "take-off" bar.

In one optional embodiment, the core may be prepared by the compression methods and apparatus described in U.S. Pat. No. 6,767,200, the disclosure of which is incorporated herein by reference. Specifically, the core is made using a rotary compression module comprising a fill zone, insertion zone, compression zone, ejection zone, and purge zone in a single apparatus having a double row die construction. The dies of the compression module are preferably filled using the assistance of a vacuum, with filters located in or near each die.

A transfer device can be used to transfer the compressed cores from the compression module to the shell-forming module. Such a transfer device can have the structure shown in published application U.S. 2003-0068367 A1. The transfer device comprises a plurality of transfer units attached in cantilever fashion to a belt. The transfer device rotates and operates in sync with the compression module and the shell-forming module to which it is coupled.

A shell surrounds the cores. The shell comprises one or more openings therein. The opening or openings can provide or facilitate formation of a passageway for communication between the core and the exterior of the dosage form. The openings may extend completely through the thickness of the shell to contact or extend into the core, or only partially through the shell.

The opening(s), in other words, constitute regions in which the shell material is missing or has been mechanically displaced.

The shell can be substantially unitary and continuous with the exception of the openings therein, or the shell may comprise multiple portions, e.g. a first shell portion and a second shell portion. In certain embodiments the shell or shell portions are in direct contact with the core. In certain other embodiments, the shell or shell portions are in direct contact with a subcoating that substantially surrounds the core. In embodiments in which the shell comprises a first and second shell portion, at least a first shell portion comprises openings therein.

In certain embodiments the first shell portion and second shell portion are compositionally different. As used herein, the term "compositionally different" means having features that are readily distinguishable by qualitative or quantitative chemical analysis, physical testing, or visual observation. For example, the first and second shell portions may contain different ingredients, or different levels of the same ingredients, or the first and second shell portions may have different physical or chemical properties, different functional properties, or be visually distinct. Examples of physical or chemical properties that may be different include hydrophylicity, hydrophobicity, hygroscopicity, elasticity, plasticity, tensile strength, crystallinity, and density. Examples of functional properties which may be different include rate and/or extent of dissolution of the material itself or of an active ingredient therefrom, rate of disintegration of the material, permeability to active ingredients, permeability to water or aqueous media, and the like. Examples of visual distinctions include size, shape, topography, or other geometric features, color, hue, opacity, and gloss.

In one embodiment, the dosage form of the invention comprises: a) a core containing an active ingredient; b) an optional subcoating that substantially covers the core; and c) a shell comprising first and second shell portions residing on the surface of the subcoating, the first shell portion comprising one or more openings, and the first shell portion being readily soluble in gastrointestinal fluids. As used herein, "substantially covers" shall mean at least about 95 percent of the surface area of the core is covered by the subcoating.

The use of subcoatings is well known in the art and disclosed in, for example, U.S. Pat. No. 3,185,626, which is incorporated by reference herein. Any composition suitable for film-coating a tablet may be used as a subcoating according to the present invention. Examples of suitable subcoatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Additional suitable subcoatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as Polysorbate-80, sodium lauryl sulfate and dioctyl-sodium sulfosuccinate; polycarbohydrates, pigments, and opacifiers.

The dried subcoating typically is present in an amount, based upon the dry weight of the core, from about 0 percent to about 5 percent.

The shell can be formed from a flowable material comprising solid particles suspended in a molten matrix, for example a polymer matrix. The flowable material may be completely molten or in the form of a paste. The flowable material may comprise an active ingredient dissolved in a molten material. The flowable material may comprise solid particles dispersed in a fluid carrier. Alternatively, the flowable material may be made by dissolving a solid in a solvent, which solvent is then evaporated after the molding step.

In one embodiment, solvent-based or solvent-free molding is performed by thermal cycle molding using the method and apparatus described in published application US 2003-0086973 A1, the disclosure of which is incorporated herein by reference. Thermal cycle molding is performed by injecting a flowable material into a heated molding chamber. The flowable material may comprise active ingredient and a thermoplastic material at a temperature above the set temperature of the thermoplastic material but below the decomposition temperature of active ingredient. The flowable material is cooled and solidifies in the molding chamber into a shaped form (i.e., having the shape of the mold).

Figure 3:
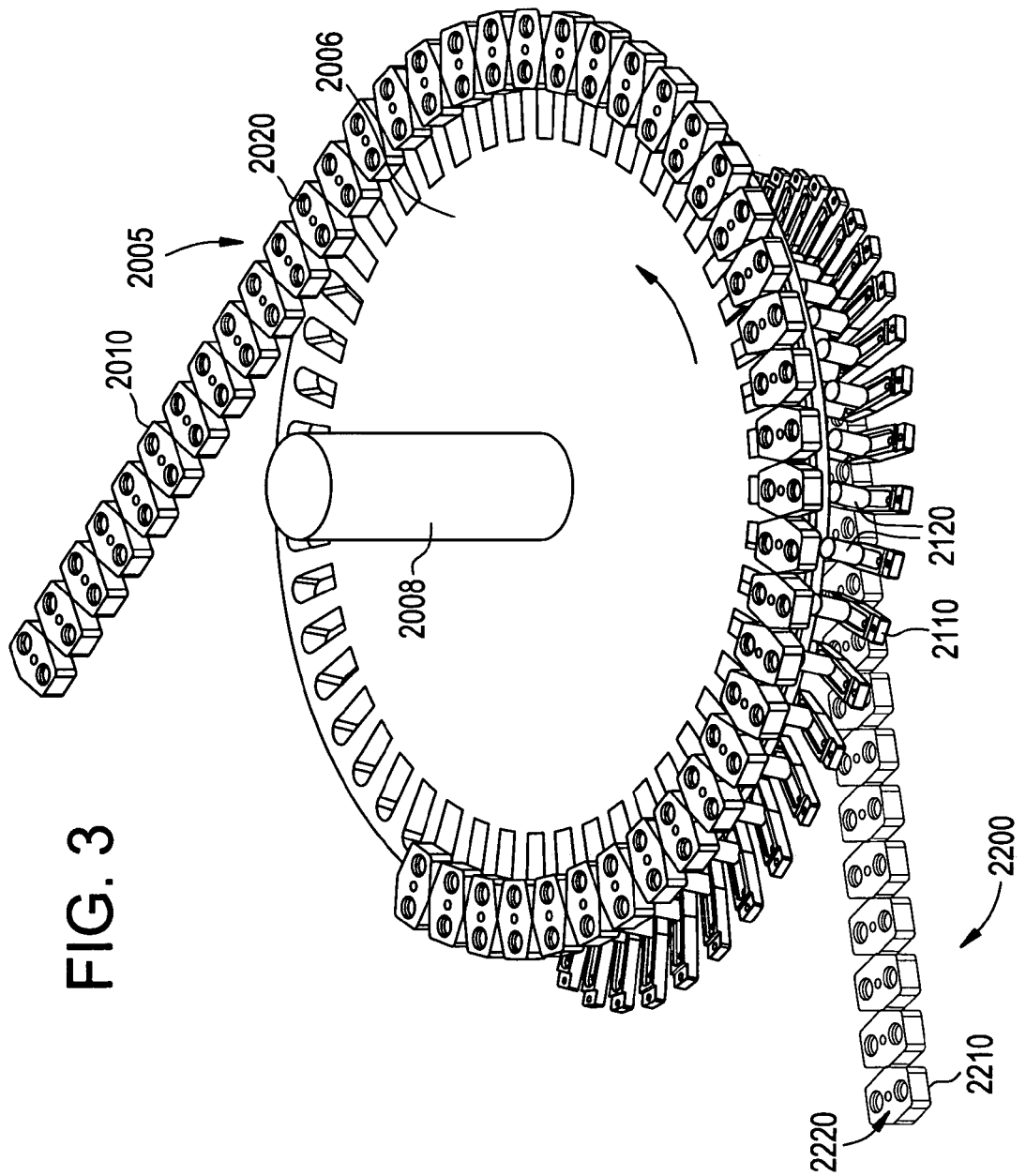
FIG. 3 illustrate a soft dosage form conveyor line and a carrier therefore useful for the practice of the present invention.

In the thermal cycle molding method and apparatus of published application US 2003-0086973 A1 a thermal cycle shell-forming module having the general configuration shown in FIG. 3 therein is employed. The thermal cycle shell-forming module comprises a rotor around which a plurality of mold units is disposed. The thermal cycle shell-forming module includes a reservoir for holding flowable material. In addition, the thermal cycle shell-forming module is provided with a temperature control system for rapidly heating and cooling the mold units.

One form of the shell-forming module useful for the practice of this invention comprises center mold assemblies, upper mold assemblies, and lower mold assemblies. Upper mold assemblies and lower mold assemblies mate to form mold cavities having a desired shape, for instance of a core or a shell surrounding one or more cores. As rotor rotates, opposing center and upper mold assemblies or opposing center and lower mold assemblies close. Flowable material, which is heated to a flowable state in reservoir, is injected into the resulting mold cavities. The temperature of the flowable material is then decreased, hardening the flowable material. The mold assemblies open and eject the shell-coated substrate. Preferably the shell is in a somewhat soft or non-brittle state, and will be hardened upon further processing, e.g. drying, etc.

In another optional embodiment of the invention, the shell is applied to the dosage form using a zero cycle molding apparatus of the general type shown in copending U.S. application Ser. No. 10/677,984 comprising rotatable center mold assemblies, lower mold assemblies and upper mold assemblies. Cores are continuously fed to the mold assemblies. Shell flowable material, which is heated to a flowable state in reservoir, is injected into the mold cavities created by the closed mold assemblies holding the cores. The mold assemblies open and eject the coated substrates. Shell coating is preferably performed in two steps, each half of the cores being coated separately.

Figure 2:
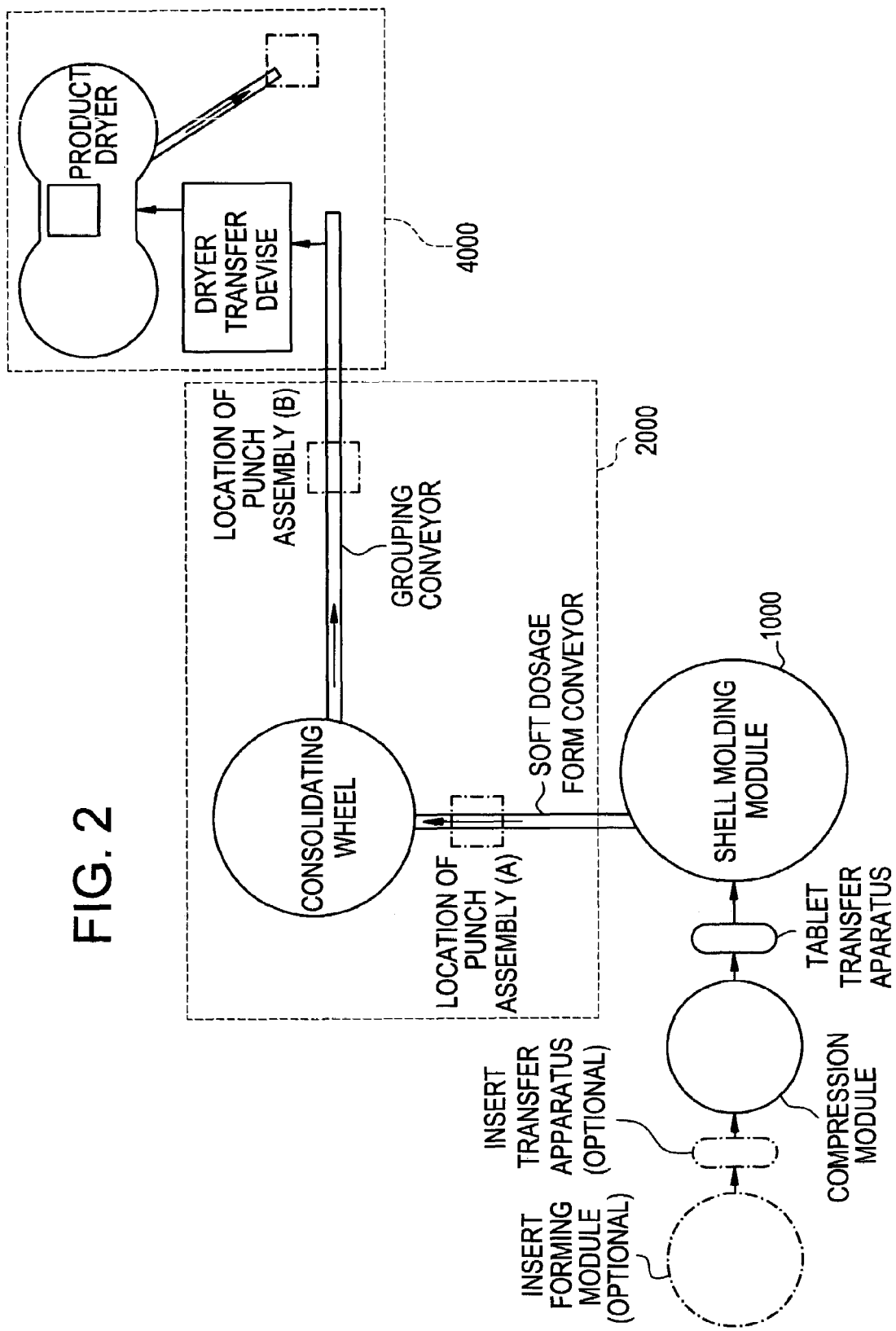
FIG. 2 is a schematic diagram of the processes and systems associated with the present invention.

The primary steps of the present invention are shown in FIG. 2 having a shell-forming module 1000, a post-coating transfer module 2000, and a drying module 4000. As previously described, the coated, hydrated and/or impressionable unfinished dosage form (soft dosage form) 100 is ejected from shell-forming module 1000 using a pin or plunger as an ejection means.

After ejection, one or more openings 130 are provided in shell 120 prior to subjecting the shell to a hardening step, such as a drying step, or otherwise allowing the shell to cure, set-up or harden. In other words, one or more openings 130 are provided in shell 120 while it is still in its hydrated and/or impressionable state. Hydrated means, for purposes of this application, having a water content at least 20% greater than its moisture content at equilibrium under ambient conditions, e.g. 25° C., 60% relative humidity.

Gelatin-based films such as those used in certain preferred coatings in the present invention or those used in hard gelatin capsules, for example, typically have a preferred moisture content at equilibrium in the range of 13-16% by weight. Additionally, gelatin capsules are considered soft and likely to distort when the moisture content is equal to or greater than 18% by weight. Hard Capsule Development, pp. 77-78, K. Ridgway (1987).

Gelation, as used herein, is initiation of formation of a polymeric or interconnecting network in an aqueous or solvent based system in which the polymer(s) are dispersed. Full cure is the highest possible degree of cure for the particular polymeric or hardenable material. Cure, as used herein is as a process for changing the properties, e.g. hardness, deformability, brittleness, elasticity, tensile strength, and the like of a resin or polymer or polymeric mixture or dispersion via chemical reaction, drying, or other physical change. Typically, a resin or polymer will exhibit an increase in viscosity or hardness during the curing process. Consequently, "full cure" would be the point at which the polymer or resin exhibits greatest viscosity and/or hardness. In embodiments employing thermal gelling materials, impressionable means, for purposes of this application, that the shell coating has passed the point of gelation so that in the absence of external force, the shell retains its shape, but has not achieved full cure. In embodiments employing non-gelling materials, such as non-solvent based melts, impressionable, as used herein means the applied shell or coating or portion thereof has cooled below it's melting temperature, so that in the absence of external force, the shell retains its shape, but has not achieved it's maximum hardness, i.e. resistance to indentation.

The term "soft dosage form" shall be used herein to mean a dosage form having a shell coating that is hydrated, impressionable or both.

In one embodiment, transfer module 2000 comprises a series of conveyors and associated transfer units that move soft dosage form 100 from shell-forming module 1000 to a "punching position" and then onwards to drying module 4000.

Post-coating transfer module 2000 receives soft dosage form 100 from shell-forming module 1000. Transfer module 2000 comprises, in one embodiment, a moving soft dosage form conveyor line 2005 having carriers 2010 shown in FIG. 3. The carriers on soft dosage form conveyor line 2005 follow a path, that includes one or more portions running along pulley wheels 2006, and that conforms to a portion of the perimeter of mold units for shell-forming module 1000 and runs at a speed synchronous with shell-forming module 1000. Pulley wheel 2006 engages each carrier 2010 and is caused to rotate by forces acting on axle 2008.

Figure 4:
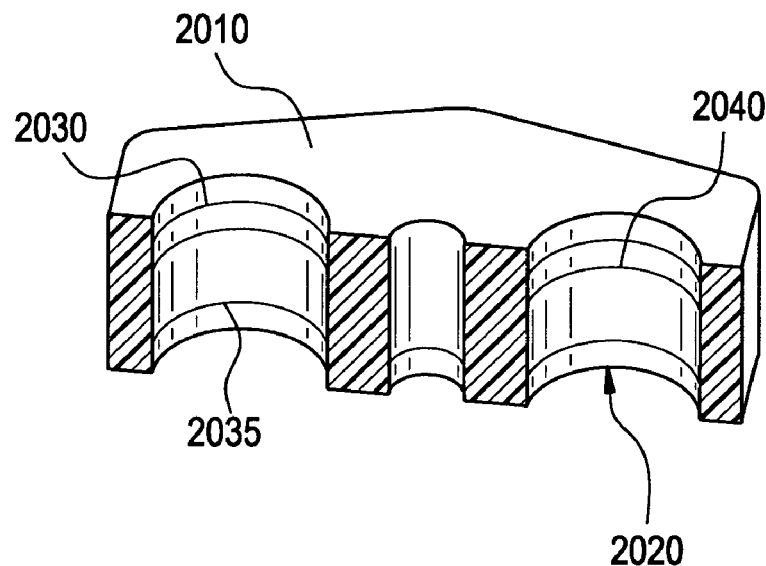
FIGS. 4 and 4a illustrate a carrier useful for the practice of the present invention.
Figure 4A:
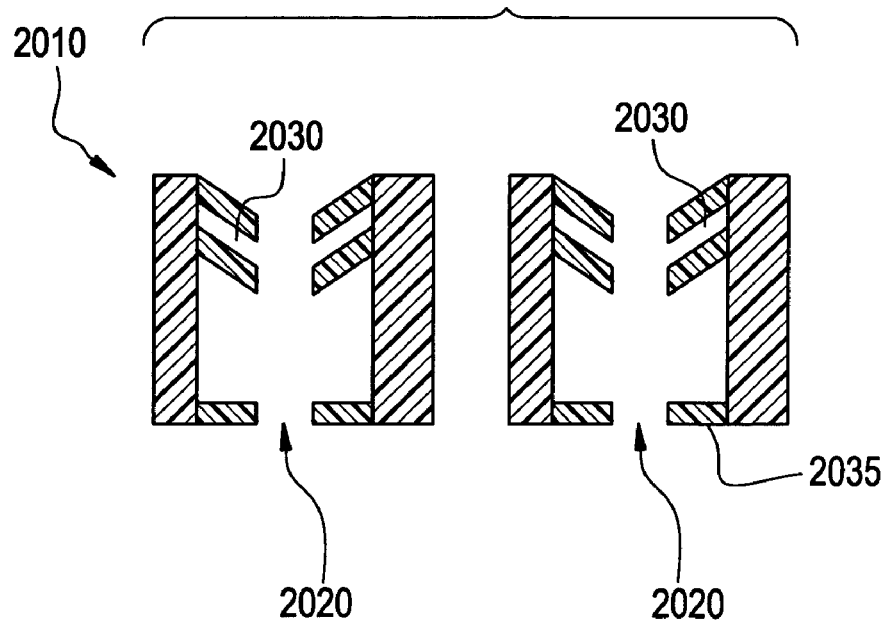

Each carrier 2010 has one or more channels 2020 that are larger in diameter than a soft dosage form, and provide an opening through both ends, e.g. top and bottom, of carrier 2010. See FIGS. 4 and 4a. Each channel 2020 has an upper liner 2030 and a lower ring 2035. Upper liner 2030 can be one or more downward-sloped elastomeric rings or alternatively fingers that grip soft dosage form 100. Upper liner 2030 allows soft dosage form 100 to be ejected from shell-forming module 1000 and pressed into a dosage form compartment 2040 formed by channel 2020 and upper liner 2030. In a preferred embodiment, each carrier 2010 comprises multiple, for example 2, channels 2020. Each carrier, excluding upper line 2030 and lower ring 2035, is preferably made in conventional fashion by machining a selected metallic material. Other materials, such as polymers, could be utilized in machining or molding processes.

Figure 5:
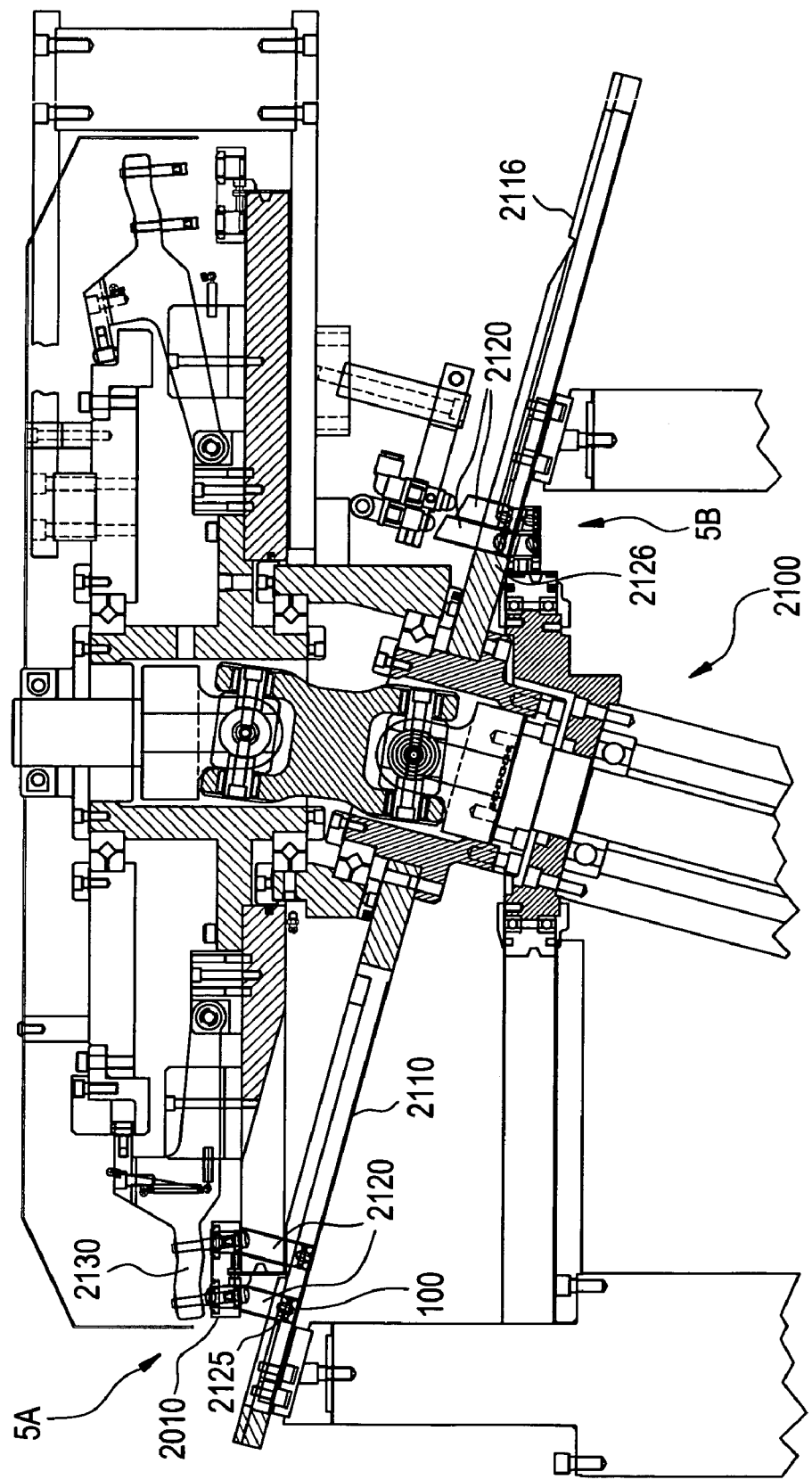
FIG. 5 illustrate a consolidating wheel useful for the practice of the present invention.

In one embodiment, carrier 2010 moves soft dosage forms 100 from shell-forming module 1000 to a consolidating wheel 2100 shown in FIGS. 2 and 5. Consolidating wheel 2100 slows the speed of and reduces the distance between soft dosage forms 100. Consolidating wheel 2100 comprises radially oriented slats 2110, and a plurality of carrier tubes 2120. Slats 2110 enable carrier tubes 2120 to move in a circular and preferably sloped direction from the receipt of soft dosage forms 100 to ejection thereof. The sloped configuration of consolidating wheel 2100 is a space efficient means for changing the elevation of soft dosage forms 100 but is by no means the only configuration available for this purpose.

Each slat 2110 conveys one or more carrier tube 2120 and more preferably at least two carrier tubes 2120 that are moveable from periphery 2125 to center region 2126 of consolidating wheel 2100 and back again. Carrier tubes 2120, which are provided on each slat 2110, move relative to one another and relative to the center of consolidating wheel 2100. Consolidating wheel 2100 has a radius that is calculated based on the velocity differential between soft dosage forms 100 coming from shell forming module 1000, and the velocity of soft dosage forms 100 in the subsequent unit operation, or (in embodiments where multiple conveyors are employed to move the dosage forms to the next unit operation) on the subsequent conveyor.

Once carriers 2010 reach a designated point over consolidating wheel 2100, soft dosage forms 100 are pushed by ejector pin and/or pressurized air through the bottom of dosage form compartment 2040, into carrier tubes 2120. One dosage form is positioned in each carrier tube 2120. Consolidating wheel 2100 rotates as carrier tubes 2120 move from an outer ring or periphery of consolidating wheel 2100 toward the center of consolidating wheel 2100, thereby effectively reducing the linear velocity and reducing the (circumferential) distance between soft dosage forms 100. In preferred embodiments employing 2 or more independently movable carrier tubes 2120 per slat 2110, the radial distance between soft dosage forms 100 is reduced by reducing the distance between the 2 carrier tubes 2120. Carrier tubes 2120 each have a portion positioned in a groove in slat 2110, and an attached cam follower portion, positioned in a cam track beneath consolidating wheel 2100. Carrier tubes 2120 are caused to move along a groove in slat 2110 toward the center of consolidating wheel 2100 by the path of the cam track as the consolidating wheel rotates.

Consolidating wheel 2100 is capable of modifying the velocity of dosage forms 100 and, as exemplified, comprises an apparatus having a rotating turret and a plurality of slats for holding individual dosage form carriers. Each slat preferably comprises two carrier tubes, wherein the carrier tubes move from the outer periphery of the rotating turret towards the center of the rotating turret. The turret is driven by an engine at a specified speed relative to the associated conveyor systems. The diameter of each carrier like 2120 is preferably larger than the diameter of the dosage form, e.g. at least about 2 times the thickness or width of the dosage form, yet smaller than one-half the distance between the outer edges of soft dosage form compartments 2040.

Dosage forms 100 are released from consolidating wheel 2100 and carrier tube 2120 from the end opposite from which dosage forms 100 entered carrier tubes 2120, into a grouping conveyor line 2200 having grouping carriers 2210. A section of grouping conveyor line 2200 and a series of carriers 2210 are shown in FIG. 3 and illustrated schematically in FIG. 2. In a preferred embodiment, each group carrier 2210 comprises multiple, for example 2, dosage form compartments 2220.

Figure 6:
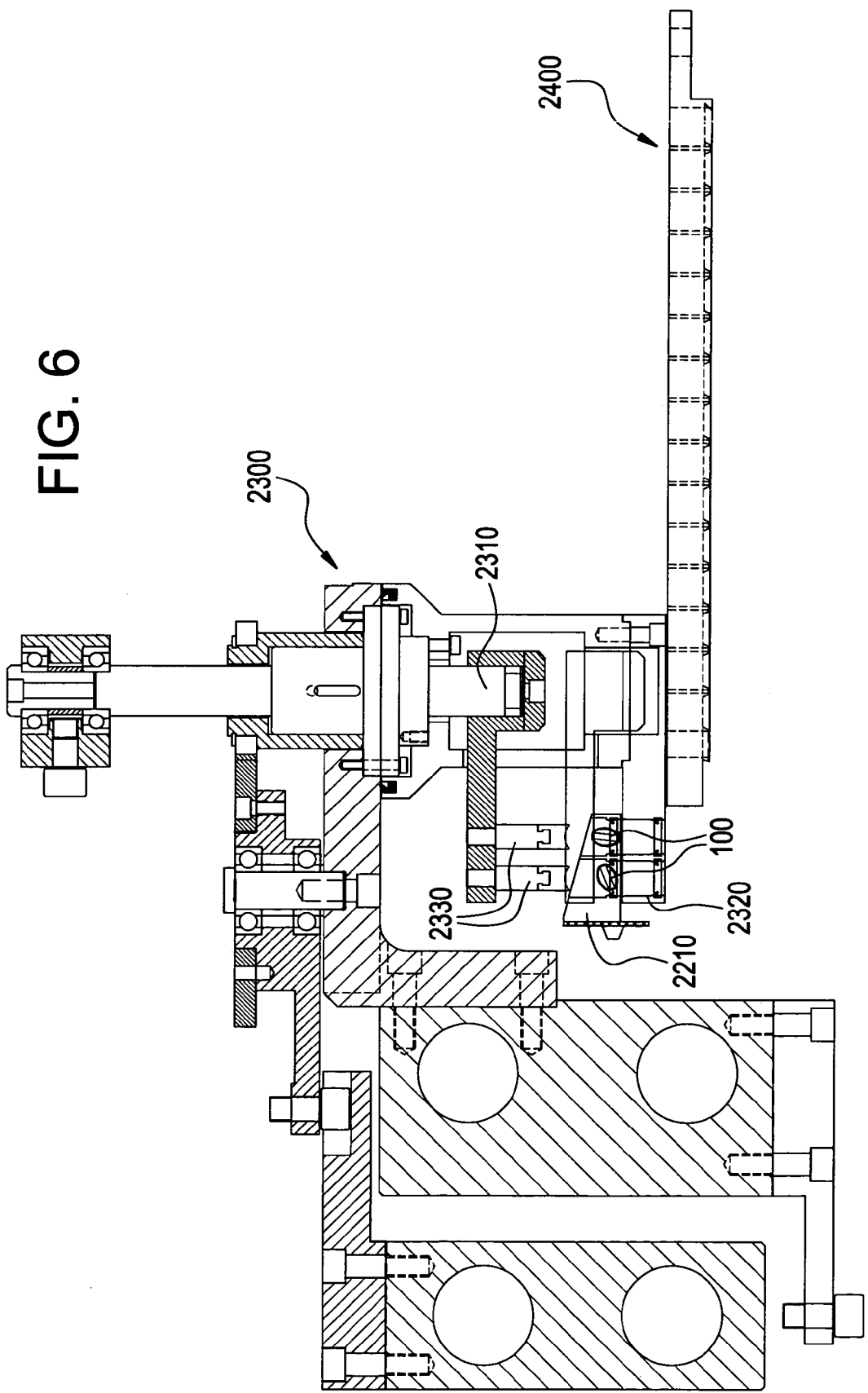
FIG. 6 illustrates a dryer transfer device and a tray capable of containing a plurality of dosage forms useful for the practice of the present invention.

Grouping conveyor line 2200 moves carriers 2210 along a path more slowly than carriers 2010 of soft dosage form conveyor line 2005. In a preferred embodiment, grouping conveyor line 2200 moves the pairs of soft dosage forms 100 into position for further transfer by a dryer transfer device 2300 into a tray 2400 capable of containing a plurality of dosage forms, shown in FIG. 6, for example 20 rows of 15 dosage forms, and to further slow their velocity. Tray 2400 is commercially available.

A dryer transfer device 2300, such as a walking beam, follows along grouping conveyor line 2200 for a period of time at the same speed as dosage form carriers 2210, receives a specified number (for example 15) of dosage forms 100 from carriers 2210, stops moving forward, and pivots to place dosage forms 100 into one or more rows of tray 2400. Dryer transfer device 2300 receives dosage forms 100 from each carrier 2210 preferably by action of a mechanical punch 2310 and/or forced air. Mechanical punch 2310 forces dosage form 100 from carrier 2210 into transfer carrier 2320. A plurality of filled transfer carriers 2320 pivot over tray 2400 along with individual punches 2330. Once in position over a desired location in tray 2400, individual punches 2330 force dosage forms 100 into the underlying tray 2400.

Dryer transfer device 2300 functions to further decrease the velocity of the dosage forms as it places a plurality, e.g. 15 at a time, into drying trays 2400. Tray 2400 is conveyed along a dryer conveyor line 4010 from that point into a drying system 4000. Dryer transfer device 2300, then returns to its original position, resumes moving along with carriers 2210, and repeats the process. The process is repeated for each tray 2400 such that optimally each position within every row contains a single dosage form 100.

In review, one embodiment of the post-coating transfer module 2000 has been described above as having soft dosage form conveyor line 2005, consolidating wheel 2100, grouping conveyor line 2200 and dryer transfer device 2300. Each of the foregoing conveyor lines can be broken up into multiple parallel or series segments. Similarly, multiple consolidating wheels 2100 could be used in series or parallel for its intended purposes. One advantage of the post-coating transfer module described above is the individual handling of soft dosage form 100 from beginning to end. Such handling is important when working with soft dosage forms. Without departing from individual handling, it would be possible to utilize a series of conveyor lines having sequentially slower speeds.

Figure 7:
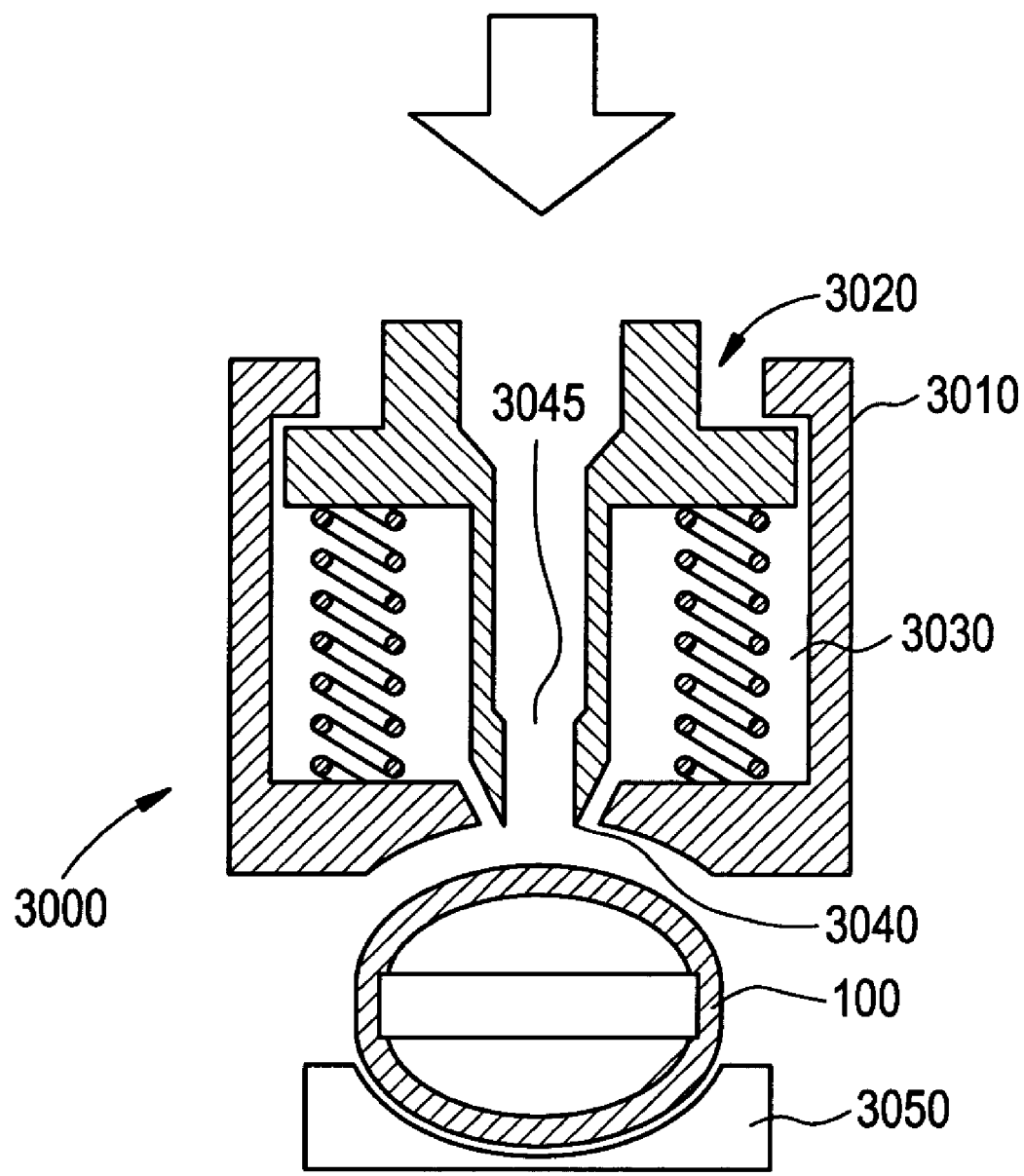
FIG. 7 illustrates a punch assembly useful for the practice of the present invention.

A punch assembly 3000 is preferably provided before the soft dosage forms 100 enter drying module 4000. However, punch assembly could be provided along dryer conveyor line 4010. Punch assembly 3000 punches the desired opening(s) 130 in soft shell 120. Dosage form 100 is positioned under punch assembly 3000 shown in FIG. 7. Punch assembly 3000 can be positioned substantially anywhere along the path of the post-coating transfer module 2000.

Two exemplary non-limiting locations are shown in FIG. 2. In one embodiment, punch assembly 3000 is positioned along soft dosage form conveyor line 2005 as embodiment A. Alternatively, punch assembly 3000 is positioned along grouping conveyor line 2200 as embodiment B. In yet another embodiment, punch assembly 3000 is positioned along a further rotary conveying module between grouping conveyor line 2200 and dryer transfer device 2300. In yet another embodiment, one or a plurality of punch assemblies 3000 are positioned on dryer transfer device 2300, e.g. on a "walking beam". Those skilled in the art will recognize that ablative methods, such as laser, could be employed to create openings in the soft dosage form at similar points along the path of the post-coating transfer module 2000.

Punch assembly 3000 comprises a spring-loaded stripper plate 3010, a punch 3020, and a spring 3030. Stripper plate 3010 prevents soft dosage form 100 from being removed from its carrier and helps prevent the shell from peeling back from the core during punching. For embodiments A and B noted above, either carrier plate 2010 or grouping carrier 2210 conveys dosage form 100 into the punching position. Dosage form 100 is carried along in a dosage compartment and retained in position due to frictional engagement with an inner elastomeric ring or set of rings. Elastomeric rings provide sufficient frictional force to overcome the force of gravity and retain dosage forms in position during movement.

Punch 3020 includes a punch tip 3040 that can have the exterior shape of the desired opening and an interior bore 3045 that is shaped to allow for the cut-out shell pieces to be pushed up through the center of the punch. A vacuum can be provided to assist in the removal of material from interior bore 3045 during and/or after the cutting operation. It is not desirable for dosage forms 100 to be released from the carriers during the punching operation. Stripper plate 3010 prevents any movement up and out from the carrier.

As punch 3020 moves into a striking position, a dosage form support plate 3050 moves into the channel containing dosage form 100. Dosage form support plate 3050 prevents dosage form 100 from being ejected from the carrier due to the force of punch 3020 and optionally reposition dosage form 100 to expose a portion to be struck. Spring 3030 provides tension to hold the stripper plate in place against the portion of the shell that is not being removed, as the punch pulls back and removes a portion of the shell covering to create opening 130.

Punch 3020 and dosage form support plate 3050 may be activated and caused to move by a variety of known mechanical means. In one embodiment, punch 3020 and support plate 3050 are squeezed together between compression rollers similarly to the upper and lower punches on a rotary tablet press. The same mechanical punch activating means moves punch 3020 back to its original position after the opening(s) is formed. In one optional embodiment, dosage form support plate 3050, may be replaced by a second punch assembly 3000 comprising second punch 3020, stripper plate 3010, and spring 3030, in order to simultaneously create openings on both faces of the soft dosage form. In this embodiment, simultaneous punch assemblies provide opposing forces that prevent any movement of soft dosage form 100 in the carrier. In a still further embodiment, sequential and opposing combinations of punch assemblies and dosage form support plates are utilized to provide openings on the same and/or opposite faces of soft dosage form 100.

In embodiments resulting in openings having substantially rounded portions, punch 3030 can be rotated for a portion of a circle during punching to utilize horizontal shear force to supplement the downward forces acting to cut the shell. Each opening may have dimensions, e.g., length, width, or diameter, in the range of about 0.1% to about 100%, of the diameter of the dosage form, or of any dimension (e.g. diameter, length, or width) of a major face of the dosage form. The diameter or width of each opening is preferably from about 0.5% to about 5% of the diameter of the dosage form, or of any dimension (e.g. diameter, length, or width) of a major face of the dosage form. In certain embodiments the diameter or width of the openings may range from about 200 to about 2000 microns. The length of the openings may range from about 1% to about 100% of the diameter of the dosage form, or of the diameter of a major face of the dosage form. In certain particular embodiments, the length or diameter of a major face of the dosage form is from about 10,000 to about 20,000 microns. In one particular embodiment, the length of the openings is from about 100 to about 20,000 microns.

The depth of the openings is typically from about 75% to about 125% of the thickness of the shell at the location of the openings. Greater than 100% thickness means that the opening is provided entirely through the shell and any optional intermediate layers, and into the core. Less than 100% means that the "opening" does not extend entirely through the shell but forms an indentation or pressed indentation. In certain embodiments, the thickness of the shell at the location of the openings typically ranges from about 20 to about 800 microns, e.g. from about 100 to about 400 microns. In one particular embodiment, the depth of the openings is from about 75 to about 400 microns. If a plurality of openings is present, they are typically spaced from one another by at least about one half, e.g. at least about one, times the smallest dimension of the smallest opening. The openings may have a variety of shapes, or be arranged in a variety of different patterns, and may have similar or different sizes.

In one embodiment, the size of the openings is small enough to prevent the core from being tasted, yet the number of openings is large enough to provide communication between a certain percentage of surface area of the core and the exterior of the dosage form.

Figure 8:
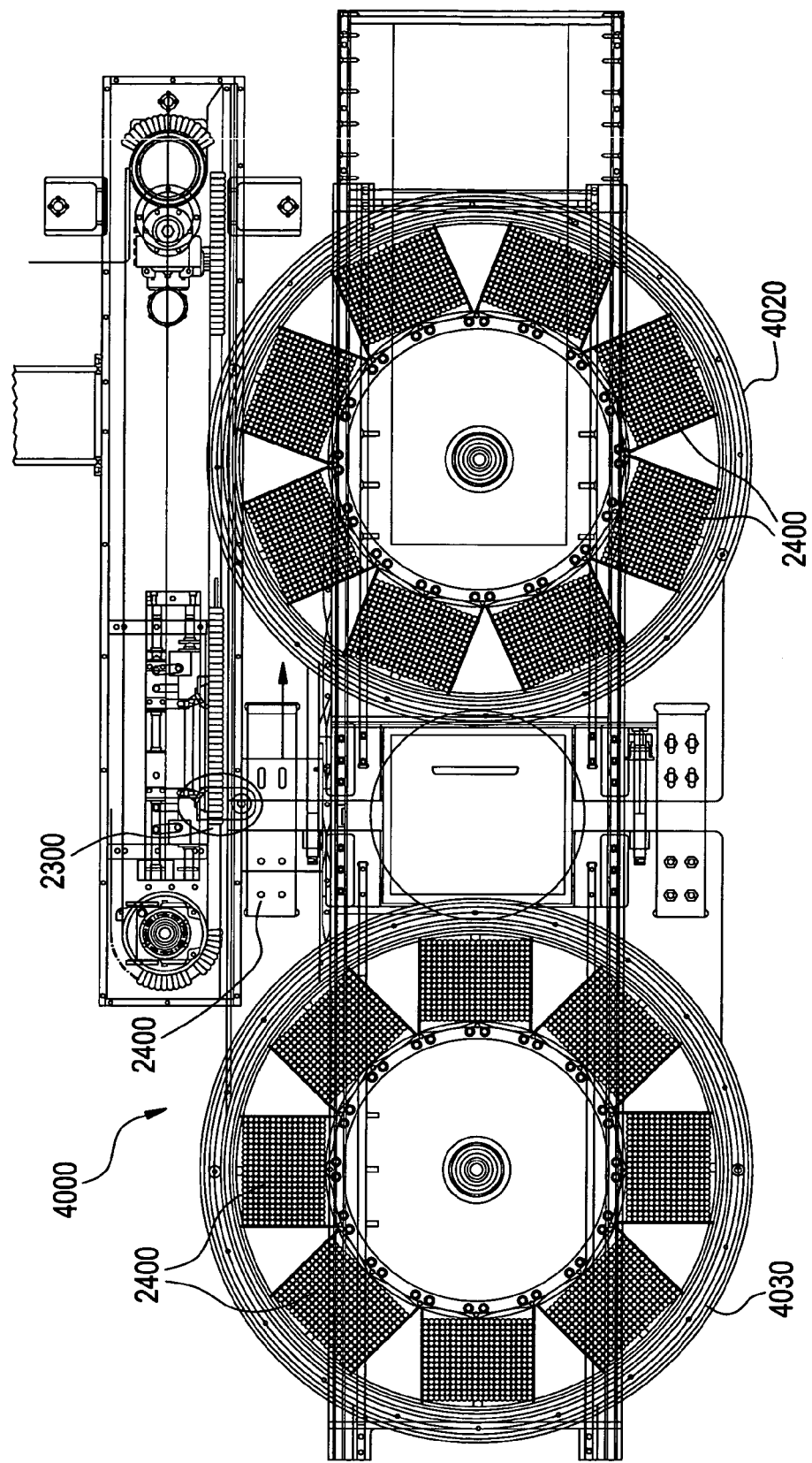
FIG. 8 illustrates a drying conveyor mechanism and drying columns for dosage forms.
Figure 9:
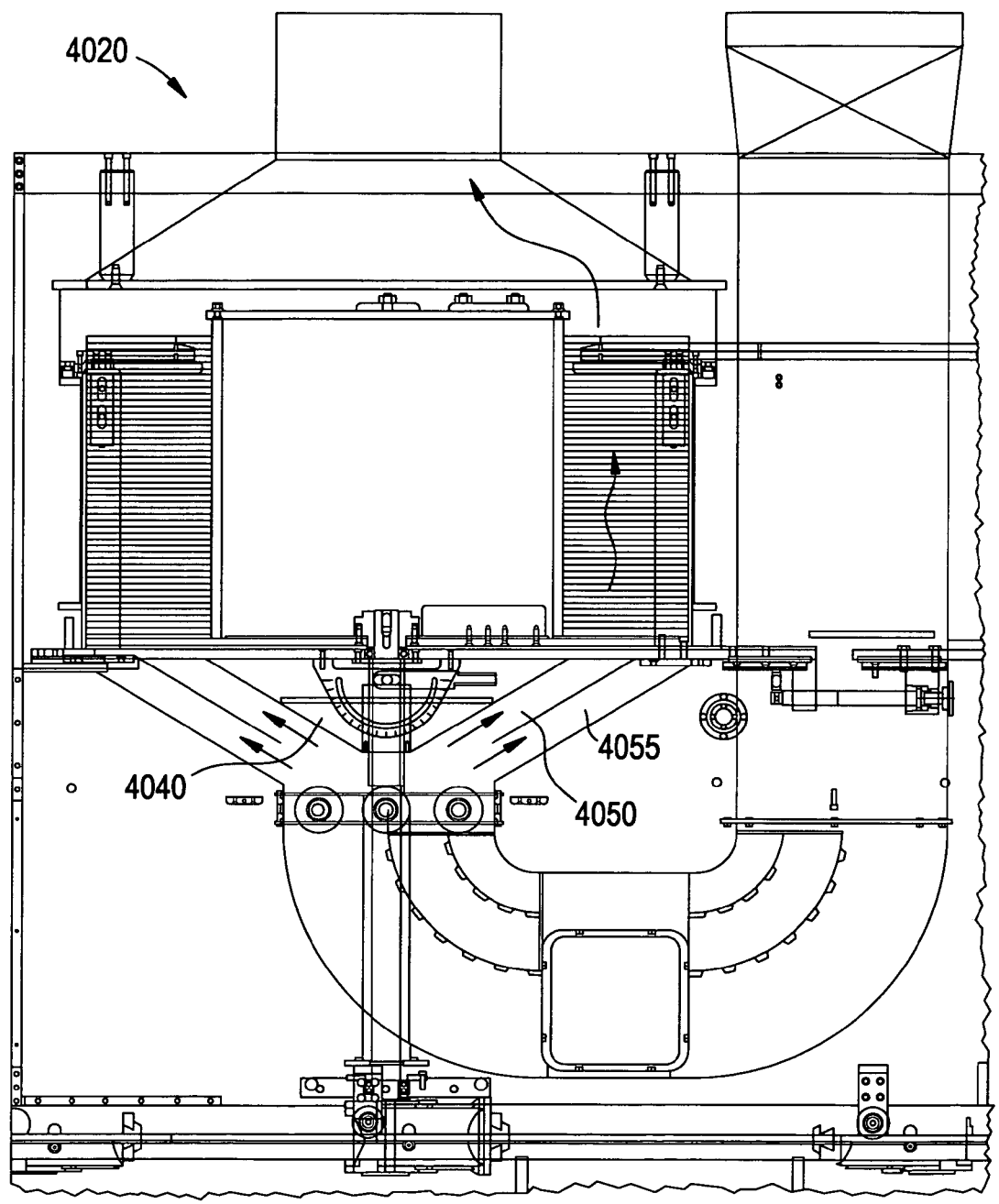
FIG. 9 illustrates a distributor for airflow in drying columns useful for the practice of the present invention.

Drying system 4000 comprises a drying conveyor mechanism 4010 for trays 2400, each carrying a plurality (e.g. 15×20) of soft dosage forms 100. Drying conveyor mechanism conveys trays 2400 containing a plurality of dosage forms 100 through first (ascending) and second (descending) dryer columns 4020 and 4030 shown in FIG. 8. Drying conveyor mechanism follows a path that spirals upward through an ascending dryer column 4020, moves horizontally to descending dryer column 4030 then spirals downward through descending dryer column 4030. Trays 2400 discharge dried dosage forms and ultimately return to receive soft dosage forms 100 from dryer transfer device 2300.

Air flows from the bottom to the top of drying system 4000, advantageously providing the driest air to the wettest dosage forms entering the bottom of ascending dryer column 4020, and to the driest dosage forms as they exit from the bottom of descending dryer column 4030. Air entering ascending dryer column 4020 and descending dryer column 4030 is distributed via a distributor 4040 comprising concentric cones 4050 and 4055. Distributor 4040 is moveable in the vertical direction to modulate the flow of air through concentric cones 4050 and 4055 by restricting or increasing the flow of air through inner cone 4050 and consequently causing outer cone 4055 to receive more or less air, respectively. Concentric cones 4050 and 4055 direct a portion of the airflow toward the periphery of the columns in order to promote more even drying across the entire tray area.

I claim:

1. A system for manufacturing a dosage form that comprises a core and a shell surrounding at least a portion of the core and having one or more openings comprising:
   a shell-forming module that overcoats at least a portion of the core with a soft shell;
   a post-coating transfer module for conveying a soft dosage form from the shell-forming module; and
   a punch assembly for producing at least one opening in the soft shell.

2. The system according to claim 1 further comprising a hardening module for substantially solidifying the shell.

3. The system according to claim 2 in which said hardening module comprises a drying module for substantially eliminating moisture from the shell.

4. The system according to claim 1 wherein the post-coating transfer module comprises a substrate velocity modifying means that enables a controlled transfer of individual substrates between two unit operations that convey individual substrates at different velocities.

5. The system according to claim 1 wherein the post-coating transfer module comprises a first dosage form conveyor from the shell-forming module, a substrate velocity modifying means for modifying the velocity of dosage forms received from the first dosage form conveyor and a second dosage form conveyor from the substrate velocity modifying means.

6. The system according to claim 3 wherein a transfer arm moves dosage forms from said second conveyor to a third conveyor into a dryer unit.

7. The system according to claim 4 wherein the substrate velocity modifying means comprises a rotating turret having a plurality of slats for holding individual dosage form carriers.

8. The system according to claim 5 wherein each slat comprises two carrier tubes.

9. The system according to claim 6 wherein the carrier tubes move from the outer periphery of the rotating turret towards the center of the rotating turret.

10. The system according to claim 6, wherein the carrier tubes move closer to one another radially.

11. The system according to claim 1, wherein one or more openings contact the core.

12. The system according to claim 1, wherein the soft shell has a water content at least 20% greater than its moisture content at equilibrium at 25° C. and 60% relative humidity.

13. The system according to claim 1, wherein the core comprises at least one active ingredient.

14. The system according to claim 10, wherein the dosage form provides for immediate release of at least one active ingredient contained in the core.

15. The system according to claim 1, wherein the core comprises a compressed tablet.

16. The system according to claim 1, wherein the compressed tablet has a hardness from about 1 to about 30 kp/cm2.

17. The system according to claim 1, wherein the shell comprises gelatin.

18. The system according to claim 1, wherein the average thickness of the shell, excluding uncoated or exposed areas of the core, is in the range from about 100 to about 400 microns.

19. The system according to claim 1, wherein the diameter or width of the one or more openings is from about 200 to about 2000 microns.

20. The system according to claim 1, wherein the post-coating transfer module conveys a soft dosage form from the shell-forming module to the punch assembly for producing at least one opening in the soft shell.

21. The system according to claim 5, wherein the punch assembly is located along the path of the first dosage form conveyor.

22. The system according to claim 5, wherein the punch assembly is located adjacent to the means for modifying dosage form velocity.

23. The system according to claim 5, wherein the punch assembly is located along the path of the second conveyor.

24. The system according to claim 6, wherein the punch assembly is located along the path of the third conveyor.

* * * * *